(12) United States Patent
Friedman

(10) Patent No.: US 6,264,949 B1
(45) Date of Patent: Jul. 24, 2001

(54) NONINVASIVE AGENTS FOR DIAGNOSIS AND PROGNOSIS OF THE PROGRESSION OF FIBROSIS

(75) Inventor: Scott L. Friedman, Scarsdale, NY (US)

(73) Assignee: Mount Sinai School of Medicine of New York University, New York, NY (US)

(*) Notice: Subject to any disclaimer, the term of this patent is extended or adjusted under 35 U.S.C. 154(b) by 0 days.

(21) Appl. No.: 09/406,641

(22) Filed: Sep. 27, 1999

Related U.S. Application Data

(60) Provisional application No. 60/102,232, filed on Sep. 29, 1998.

(51) Int. Cl.$^7$ .......................... A61K 39/395; A61K 51/00; A61K 38/00
(52) U.S. Cl. .................... 424/133.1; 424/1.49; 424/1.69; 424/9.1; 424/9.34; 424/9.4; 424/9.6; 424/134.1; 424/142.1; 424/143.1; 424/178.1; 435/7.21; 514/2
(58) Field of Search ........................... 435/7.21; 436/804; 424/1.49, 133.1, 134.1, 142.1, 143.1, 178.1, 1.69, 9.1, 9.34, 9.4, 9.6; 514/12, 2

(56) References Cited

U.S. PATENT DOCUMENTS 5,441,050  8/1995  Thurston et al. .
5,468,468 * 11/1995  LaRochelle et al. .

FOREIGN PATENT DOCUMENTS

WO/00/23113  4/2000  (WO) .

OTHER PUBLICATIONS

Abdel–Aziz G., et al. 1990. Reversibility of hepatic fibrosis in experimentally induced cholestasis in rat. Am J Pathol. 137(6):1333–42.
Belijaars, L. 1999. Novel drug carriers for targeting to hepatic stellate cells: new directions for antifibrotic therapies. Ponsen, Looigen BV, Wageningen, The Netherlands. Chapter 8.
Belijaars, L. et al. 1999 Albumin modified with mannose 6–phosphate: A potential carrier for selective delivery of antifibrotic drugs to rat and human hepatic stellate cells. Hepatology. 29(5):1486–93.
Clements et al. 1991. Two PDGF–B chain residues, arginine 27 and isoleucine 30, mediate receptor binding and activation. EMBO J. 10(13):4113–20.
Couser WG. 1993 Pathogenesis of glomerulonephritis. Kidney Int Suppl. 42:S19–26.
Franklin et al. 1990. In situ distribution of the beta–subunit of platelet–derived growth factor receptor in nonneoplastic tissue and in soft tissue tumors. Cancer Res.; 50(19):6344–8.
Friedman SL. 1993. Seminars in medicine of the Beth Israel Hospital, Boston. The cellular basis of hepatic fibrosis. Mechanisms and treatment strategies. N Engl J Med. 328(25):1828–35.

Friedman SL. 1996. Hepatic stellate cells. Prog Liver Dis. 14:101–30.
Gay S, et al. 1989. Immunohistologic demonstration of platelet–derived growth factor (PDGF) and sis–oncogene expression in scleroderma. J Invest Dermatol. 92(2):301–3.
Handmaker H. 1994. Peptide tracers excel at disease localization. Diagn Imaging (San Franc), Nov.;16(11):77–8, 81–3, 171.
Hart et al. 1987. Synthesis, phosphorylation, and degradation of multiple forms of the platelet–derived growth factor receptor studied using a monoclonal antibody. J Biol Chem. 262(22):10780–5.
Hart et al. 1988. Two classes of PDGF receptor recognize different isoforms of PDGF. Science. 240(4858):1529–31.
Hines JE, et al., 1993. In vivo responses of macrophages and perisinusoidal cells to cholestatic liver injury. Am J Pathol. 142(2):511–8.
Huang, JS et al. 1982, Platelet–dervived growth factor. Specific binding to target cells. J Biol Chem. 257(14):8130–6.
Iida et al. 1991. Platelet–derived growth factor (PDGF) and PDGF receptor are induced in mesangial proliferative nephritis in the rat. Proc Natl Acad Sci U S A. 88(15):6560–4.
Iredale JP, et al. 1998. Mechanisms of spontaneous resolution of rat liver fibrosis. Hepatic stellate cell apoptosis and reduced hepatic expression of metalloproteinase inhibitors. J Clin Invest. 102(3):538–49.
Lister–James J et al. 1996. Small peptides radiolabeled with 99mTc. Q J Nucl Med. 40(3):221–33.
Lister–James J et al. 1997. Pharmacokinetic considerations in the development of peptide–based imaging agents. Q J Nucl Med. 41(2):111–8.
Mathew J, et al. 1994. Quantitative analysis of macrophages and perisinusoidal cells in primary biliary cirrhosis. Histopathology. 25(1):65–70.
Oefner C. et al. 1992. Crystal structure of human platelet–derived growth factor BB. EMBO J. 11(11):3921–6.
Patel G. et al. 1999. A cyclic peptide analogue of the loop III region of platelet–derived growth factor–BB is a synthetic antigen for the native protein. J Pept Res. 53(1):68–74.
Pinzani M, et al. 1995. Transforming growth factor–beta 1 regulates platelet–derived growth factor receptor beta subunit in human liver fat–storing cells. Hepatology. 21(1):232–9.

(List continued on next page.)

Primary Examiner—David Saunders
Assistant Examiner—Amy Decloux
(74) Attorney, Agent, or Firm—Pennie & Edmonds LLP

(57) ABSTRACT

The present invention relates to the use of molecules capable of specifically binding a β PDGFR as diagnostic reagents for the detection of fibrosis in vivo. Such fibrosis can include, but are not limited to, liver, lung, kidney, prostrate and breast fibrosis.

19 Claims, No Drawings

OTHER PUBLICATIONS

Pinzani et al. 1996. Expression of platelet–derived growth factor and its receptors in normal human liver and during active hepatic fibrogenesis. Am J Pathol. 148(3):785–800.

Poynard, T et al. 1997 Natural history of liver fibrosis progression in patients with chronic hepatitis C. The OBSVIRC, METAVIR, CLINIVIR, and DOSVIRC groups. Lancet. 349(9055):825–32.

Reeves HL. et al. 1996. Hepatic stellate cell activation occurs in the absence of hepatitis in alcoholic liver disease and correlates with the severity of steatosis. J Hepatol. 25(5):677–83.

Seifert RA et al. 1989. Two different subunits associate to create isoform–specific platelet–derived growth factor receptors. J Biol Chem. 264(15):8771–8.

Smits A, et al. 1992. Expression of platelet–derived growth factor and its receptors in proliferative disorders of fibroblastic origin. Am J Pathol. 140(3):639–48.

Sun PD and Davies DR. 1995. The cystine–knot growth–factor superfamily. Annu Rev Biophys Biomol Struct. 24:269–91.

Tazi KA, et al. 1997. Responsiveness to growth factors in aortic vascular smooth muscle cells from rats with cirrhosis. Am J Physiol. 273(4 Pt 1):G883–90.

Uebelhoer M., et al. 1995. Modulation of fibroblast activity in histiocytosis X by platelet–derived growth factor. Chest. 107(3):701–5.

Verbaan H, et al. 1997 Non–invasive assessment of inflammatory activity and fibrosis (grade and stage) in chronic hepatitis C infection. Scand J Gastroenterol. 32(5):494–9.

Ankoma–Sey V et al., "Coordinated induction of VEGF receptors in mesenchymal cell types during rat hepatic wound healing", Oncogene. Jul. 9, 1998;17(1):115–21.

Bogdanov A Jr and Weissleder R, "The development of in vivo imaging systems to study gene expression", Trends Biotechnol. Jan. 1998;16(1):5–10.

Brennand DM et al., "A cyclic peptide analogue of loop III of PDGF–BB causes apoptosis in human fibroblasts", FEBS Lett. 1997 Dec. 15, 1997;419(2–3):166–70.

Brennand DM et al., "Identification of a cyclic peptide inhibitor of platelet–derived growth factor–BB receptor–binding and mitogen–induced DNA synthesis in human fibroblasts", FEBS Lett. Aug. 11, 1997;413(1):70–4.

Friedman SL, "Molecular mechanisms of hepatic fibrosis and principles of therapy", J Gastroenterol. 1997 Jun. 1997;32(3):424–30.

Friedman SL et al., "Activation of cultured rat hepatic lipocytes by Kupffer cell conditioned medium. Direct enhancement of matrix synthesis and stimulation of cell proliferation via induction of platelet–derived growth factor receptors", J Clin Invest. Dec. 1989 84(6):1780–5.

Gressner AM, "The cell biology of liver fibrogenesis—an imbalance of proliferation, growth arrest and apoptosis of myofibroblasts", Cell Tissue Res. Jun. 1998 292(3):447–52.

Heldin CH et al., "Interaction of platelet–derived growth factor with its fibroblast receptor. Demonstration of ligand degradation and receptor modulation", J Biol Chem. Apr. 25, 1982; 25;257(8):4216–21.

Hom RK and Katzenellenbogen JA, "Technetium–99m–labeled receptor–specific small–molecule radiopharmaceuticals: recent developments and encouraging results", Nucl Med Biol. Aug.1997;(6):485–98.

McAfee JG et al., "Radiolabeled peptides and other ligands for receptors overexpressed in tumor cells for imaging neoplasms", Nucl Med Biol. Aug. 1996;23(6):673–6.

Nilsson J et al., "Surface binding and internalization of platelet–derived growth factor in human fibroblasts", Proc Natl Acad Sci U S A. Sep. 1983;80(18):5592–6.

Pinzani M et al., "Signal trasduction in hepatic stellate cells", Liver. Feb. 1998;18(1):2–13.

Rosenfeld ME et al., "Platelet–derived growth factor: morphologic and biochemical studies of binding, internalization, and degradation", J Cell Physiol. Nov. 1984;121(2):263–74.

Rusckowski M et al., "Technetium–99m labeled epidermal growth factor–tumor imaging in mice", J Pept Res. 1997 Nov. 1997;50(5):393–401.

Westermark B et al., "Structural and functional aspects of platelet–derived growth factor and its receptors", Ciba Found Symp. 1990;150:6–14.

Wong L et al., "Induction of beta–platelet–derived growth factor receptor in rat hepatic lipocytes during cellular activation in vivo and in culture", J Clin Invest. Oct. 1994;94(4):1563–9.

Franklin et al. Cancer Research 50:6344–6348, 1990.*

* cited by examiner

NONINVASIVE AGENTS FOR DIAGNOSIS AND PROGNOSIS OF THE PROGRESSION OF FIBROSIS

This application is entitled to and claims priority benefit of application Ser. No. 60/102,232 filed Sep. 29, 1998, the entire disclosure of which is incorporated herein by reference.

This invention was made with government support under grant number DK 37340 awarded by the National Institutes of Health. The government has certain rights in the invention.

1. INTRODUCTION

The present invention relates to the use of molecules capable of specifically binding a human β PDGF receptor (β PDGFR) as diagnostic reagents for the minimally invasive assessment and detection of fibrosis. The present invention relates to methods and compositions for the screening for the diagnosis and/or prognosis of fibrosis. The present invention also relates to noninvasive methods for monitoring the effectiveness of treatment of fibrosis. Such fibrosis can include, but are not limited to, liver, lung, kidney, prostate and breast fibrosis.

2. BACKGROUND

2.1. The Progression of Fibrosis

Progressive fibrosis of liver, kidney, lungs, and other viscera often results in organ failure leading to death or the need for transplantation. These diseases affect millions in the United States and worldwide. For example, hepatic fibrosis is the leading non-malignant gastrointestinal cause of death in the United States. Moreover, it has been increasingly recognized that progression of fibrosis is the single most important determinant of morbidity and mortality in patients with chronic liver disease (Poynard, T. P. et al., 1997, Lancet 349:825–832).

Currently there is no alternative to direct biopsy of affected organs to assess the extent of fibrosis. For all tissues this involves either percutaneous or transbronchial biopsy, procedures whose risks include bleeding, perforation or death. Moreover, biopsy is contraindicated in patients with end-stage diseases in whom there are clotting abnormalities.

2.2. Hepatic Fibrosis

In all tissues, activation of resident mesenchymal cells is a key event in the development of fibrosis. In the kidney, this mesenchymal cell is represented by the mesangial cell (Border, W. A., 1994, Current Opinion in Nephrology Hypertension 3:54–58) and in the liver, the hepatic stellate cell (HSC, otherwise referred to as Ito cells, fat-storing cells, lipocytes) fulfills this role. Subsequent to acute or chronic liver damage, HSC undergo activation, a process characterized by the transformation of resting cells into proliferative, fibrogenic, and contractile myofibroblast-like cells. Activated HSC contribute to the tissue repair process, namely the reconstitution of an extracellular matrix (ECM) network necessary for tissue regeneration. In cases of acute/self-limited tissue damage these changes are self-limited and effective. In contrast, cases of persistent liver injury result in chronic inflammation and lead to the accumulation of ECM. The reasons for the chronicity are not clear, but could reflect the presence of mediators unique to chronic injury, or more likely, failure of compensatory mechanisms (i.e., downregulators of inflammation, or matrix protease activity) to keep pace with the ongoing fibrosis.

A cascade of events involving soluble stimuli, matrix-related changes, and altered gene expression results in the activation of HSC. Activation consists of early ("initiation") and late ("perpetuation") phases. Early activation appears to be provoked by at least two stimuli, rapid deposition of cellular fibronectin, and release of soluble stimuli by Kupffer cells (hepatic macrophages). The late phase of activation consists of at least five discrete phenotypic changes: (1) proliferation, (2) mitogenesis, (3) contractility, (4) release of proinflammatory cytokines, and (5) matrix protease release.

Activation and proliferation of HSC in liver injury is associated with de novo expression of many cytokine receptors, including epidermal growth factor (EGF-R), transforming growth factor (TGF) β-R types I, II, and III, endothelial receptor (ET-R), vascular endothelial growth factor (VEGF)-R, thrombin-R and platelet derived growth factor (PDGF)-R (Friedman, S. L., 1997, Journal of Gastroenterology 32:424–430; Ankoma-Sey, V. M. et al., 1998, Oncogene 17:115–121; Friedman, S. L., 1989, Journal of Clinical Investigation 84:1780–1785; Wong, L. G. et al., 1994, Journal of Clinical Investigation 94:1563–1569). Moreover, HSC activation is associated with the expression of several cytokines, growth factors and inflammatory mediators, including EGF, FGF, ET-1, insulin-like growth factor (IGF), thrombin, TGF α, TGF β, hepatocyte growth factor (HGF), stem cell factor (SCF), and PDGF (Friedman, S. L., 1997, Journal of Gastroenterology 32:424–430). HSC activation is also associated with an increase in the production of extracellular matrix components, namely collagen types I, III, IV, V, VI, XIV, proteoglycans, and glycoproteins, including fibronectin, laminin, and tenascin. Furthermore, HSC activation is associated with the production of matrix proteases, including MMP-2, stromelysin-1 (transin), MMP-1 (interstitial collagenase), and MT-MMP (membrane type-matrix metalloproteinase), and protease inhibitors, including TIMP-1, TIMP-2, and PAI-1. Thus, the expression of several different factors are associated with HSC activation.

2.3. Diagnosis and Staging of Disease

While detection of markers of fibrotic disease may be useful for prognosis modalities in vitro, no reliable system currently exists for the detection of fibrosis in a patient—information which would be extremely important for staging disease and designing an appropriate clinical approach. In fact, the inability to diagnose and image fibrosis in vivo, continues to be a major obstacle to the successful treatment of cancer and inflammatory disorders. Current surgical practice commonly resorts to vision and palpation in combination with locally determined protocols dictating the extent of tissue resection. Thus, tissue removed during surgery includes not only tissue suspected by the surgeon of being fibrotic, but also includes an amount of healthy tissue taken because the precise fibrotic margins cannot be readily ascertained by the surgeon. Accordingly, there is a great need in the art for sensitive methods to reliably detect and localize metastases in vivo.

3. SUMMARY OF THE INVENTION

The present invention relates to a minimally invasive test for the diagnosis and prognosis of fibrotic disease. In accordance with the present invention, a labeled cytokine ligand which binds specifically to a receptor on mesenchymal cells is administered to a patient, the extent of binding is used as an indicator of the mass of mesenchymal cells and the extent of fibrosis and the rate of fibrogenesis. In accordance with the present invention, the labeled ligand may be administered orally or intravenously and followed by methods known in the art for in vivo scanning as described herein.

The present invention relates to methods for the diagnosis and imaging of fibrosis using labeled molecules that specifically bind a β PDGF receptor, particularly for detecting and imaging metastases in vivo. The present invention relates to methods and compositions for screening, diagnosis and prognosis of fibrosis. The present invention further relates to methods for monitoring the effectiveness of treatment of fibrosis and for drug development.

In a preferred embodiment of the invention, fibrosis in a subject are detected by: (a) administering labeled molecules which specifically bind β PDGFR; (b) permitting the labeled molecules to preferentially concentrate in one or more fibrotic lesions in the subject and unbound labeled molecule to be cleared to background level; (c) determining the background level; and (d) detecting the labeled molecule such that detection of labeled molecule above the background level indicates the presence of a fibrotic lesion.

In another preferred embodiment, the labeled molecule of the invention can be detected in a subject wherein the subject had been administered the labeled molecule at a sufficient time interval prior to detection to allow the labeled molecule to preferentially concentrate at fibrotic lesions.

In specific embodiments the labeled molecule is labeled anti-PDGF-β antibody or fragments containing the β PDGF binding domain or peptide mimetics of PDGF-β. In another specific embodiment, the labeled molecule is a peptide or derivative thereof that binds β PDGFR but does not activate nor signal the receptor.

4. DETAILED DESCRIPTION OF THE INVENTION

The present invention relates to a minimally invasive test for the diagnosis and prognosis of fibrotic disease which comprises the intraveneous administration of a labeled ligand which binds specifically to a receptor on mesenchymal cells, the extent of binding is used as an indicator of the mass of mesenchymal cells and the extent of fibrosis and the rate of fibrogenesis.

In a preferred embodiment of the present invention, a labeled PDGF-like small molecule ligand which specifically recognizes the β PDGFR, but only binds transiently and does not activate nor signal the cognate receptor, is administered to a patient to detect hepatic fibrosis in vivo. Such a labeled ligand may be used for the diagnosis and prognosis of fibrosis and disease and disorders related to hepatic fibrosis, including chronic HCV and HBV infection and cirrhosis. The present invention may also be used to monitor the effectiveness of current anti-inflammatory and anti-fibrotic therapies for these disorders, e.g., alpha interferon treatment for HCV and HBV, to serially assess fibrosis as a means to determine a patient's responsiveness to therapy and prognosis.

The development of an in vivo imaging system as described herein to assess the extent of fibrosis will enable the prognosis of a greater number of patients to be determined and will eliminate the risks associated with biopsy. Moreover, the in vivo imaging test of the present invention will reduce the costs associated with assessing the extent of fibrosis. A variety of imaging techniques are available, including positron emission tomography (PET) and SPECT scanning and magnetic resonance (MR) scanning, which may used in conjunction with markers of fibrosis as described herein.

The ligands of the present invention are described in terms of ligands of β PDGFR by way of example, and not by way of limitation. Ligands of the present invention encompass any ligand which specifically binds to, but does not stimulate, a receptor or molecule which is upregulated or activated as a result of the progression of fibrosis and fibrotic disease, including, but not limited to TGF-βR, EGFR, VEGFR, endothelial receptor (ET-R) and fibronectin.

The invention further relates to the use of molecules having binding specificity for β PDGFR for the detection, diagnosis, or monitoring in vivo, of fibrosis, preferably hepatic fibrosis. In one embodiment of the invention, the subject is injected with the molecule having binding specificity for β PDGFR. After a time sufficient to allow for distribution and accumulation in vivo, the subject can be imaged. A variety of methods can be used to detect accumulated labeled material in vivo, including but not limited to radioimaging techniques, e.g., X-ray, CAT scan, and magnetic resonance imaging (MRI), sonography, and positron emission tomography (PET).

4.1. β PDGFR Binding Molecules

Described herein are methods for the production of molecules capable of specifically recognizing one or more β PDGFR epitopes or epitopes of conserved variants or peptide fragments of a PDGF-β, including, but not limited to, antibodies, derivatives (including but not limited to fragments) and analogs thereof, and peptides and peptide mimetics.

Such β PDGFR binding molecules may be used, for example, in the detection of β PDGFR in a biological sample and may, therefore, be utilized as part of a diagnostic technique whereby subjects may be tested for abnormal levels of β PDGFR. According to one embodiment of the invention, a β PDGFR binding molecule specifically binds to the human β PDGFR.

4.1.1. Antibodies to β PDGFR, Derivatives and Analogs

Such β PDGFR binding molecules may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

Various procedures known in the art may be used for the production of polyclonal antibodies to a β PDGFR protein or fragment thereof. For the production of polyclonal antibody, various host animals can be immunized by injection with the native β PDGFR protein, or a synthetic version, or fragment thereof, including but not limited to rabbits, mice, rats, chickens, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies directed toward a β PDGFR protein sequence, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089 and Winter, U.S. Pat. No. 5,225,539, which are incorporated herein by reference in their entirety.) An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against β PDGFR. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science, 246, 1275–1281) to allow rapid and easy identification of monoclonal Fab fragments with the desired specificity.

4.1.2. Peptides, Derivatives, Analogs, and Peptide Mimetics

In an embodiment of the invention, β PDGFR binding molecules include peptides, derivatives and analogs thereof, and peptide mimetics. In particular embodiments of the invention, the peptides or peptide mimetics are selected to mimic sequences of human PDGF-β. In yet another embodiment, β PDGFR binding molecules include cyclic peptides and cyclic octapeptides which bind to the human β PDGFR.

In a specific embodiment, the methods of the invention use PDGF-β derivatives and analogs, in particular β PDGF fragments and derivatives of such fragments, that comprise one or more domains of a PDGF-β protein.

In another specific embodiment, the methods of the invention use a PDGF-β protein, fragment, analog, or derivative which is expressed as a fusion, or chimeric protein product (comprising the protein, fragment, analog, or derivative joined via a peptide bond to a heterologous protein sequence (of a different protein)). A specific embodiment relates to a chimeric protein comprising a fragment of PDGF-β of at least six amino acids.

Peptides, derivatives and analogs thereof, and peptide mimetics that specifically bind β PDGFR can be produced by various methods known in the art, including, but not limited to solid-phase synthesis or by solution (Nakanishi et al., 1993, Gene 137:51–56; Merrifield, 1963, J. Am. Chem. Soc. 15:2149–2154; Neurath, H. et al., Eds., *The Proteins*, Vol II, 3d Ed., p. 105–237, Academic Press, New York, N.Y. (1976). For example, a peptide corresponding to a portion of a PDGF-β protein which comprises the desired domain for binding to a receptor, can be synthesized by use of a peptide synthesizer. Furthermore, if desired, nonclassical amino acids or chemical amino acid analogs can be introduced as a substitution or addition into a PDGF-β sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

The PDGF-β peptides may be isolated and purified by standard methods including chromatography (e.g., ion exchange, affinity, and sizing column chromatography), centrifugation, differential solubility, or by any other standard technique for the purification of peptides.

The functional properties may be evaluated using any suitable assay, including, but not limited to, competitive and non-competitive assay systems using techniques such as radioimmunoassays, ELISA (enzyme linked immunosorbent assay), "sandwich" immunoassays, immunoradiometric assays, in situ immunoassays (using colloidal gold, enzyme or radioisotope labels, for example), western blots, immunofluorescence assays, and immunoelectrophoresis assays, etc. For example, to select antibodies which recognize a specific domain of a β PDGFR, one may assay generated hybridomas for a product which binds to a PDGF-β fragment containing such domain. In one embodiment, antibody binding is detected by detecting a label on the antibody. Many means are known in the art for detecting binding in an immunoassay and are within the scope of the present invention.

The production and use of derivatives and analogs related to PDGF-β are within the scope of the present invention. In a specific embodiment, the derivative or analog is functionally active, i.e., capable of exhibiting one or more functional activities associated with a full-length, wild-type β PDGF protein. As one example, such derivatives or analogs which have the desired antigenicity can be used, for example, in diagnostic immunoassays as described in Section 4.2. Derivatives or analogs of β PDGF can be tested for the desired activity by procedures known in the art, including but not limited to the assays described infra. In one specific embodiment, peptide libraries can be screened to select a peptide with the desired activity; such screening can be carried out by assaying, e.g., for binding to β PDGFR.

In particular, β PDGF derivatives can be made by altering PDGF-β sequences by substitutions, additions or deletions that provide for functionally equivalent molecules. The PDGF-β derivatives of the invention include, but are not limited to, those containing, as a primary amino acid sequence, all or part of the amino acid sequence of a PDGF-β peptide including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of β PDGF include but are not limited to those peptides which are substantially homologous to PDGF-β or fragments thereof.

Included within the scope of the invention are PDGF-β protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

4.2. Labeling

Described herein are methods for detectably labeling molecules capable of specifically recognizing one or more β PDGFR epitopes or epitopes of conserved variants or peptide fragments of a β PDGFR. The labeling and detection methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

One of the ways in which the β PDGFR-specific antibody or peptide mimetic can be detectably labeled is by linking the same to an enzyme, such labeled molecules can be used in an enzyme immunoassay such as ELISA (enzyme linked immunosorbent assay). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibodies, derivatives and analogs thereof, and peptides include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

For use in the detection methods of the invention, the molecules are preferably labeled with a radioisotope, including but not limited to: $^{125}I$, 131I, or $^{99m}Tc$. Such peptides and antibodies can be detected in in vivo assays using a radioimmunoassay (RIA) or radioprobe. The radioactive isotope can be detected by such means as the use of a gamma counter or a scintillation counter or by autoradiography.

It is also possible to label the antibodies, derivatives and analogs thereof, and peptides with a fluorescent compound. When the fluorescently labeled peptide is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibodies, derivatives and analogs thereof, and peptides can also be detectably labeled using fluorescence emitting metals such as $^{152}Eu$, or others of the lanthanide series. These metals can be attached to the antibodies, derivatives and analogs thereof, and peptides using such metal chelating groups as diethylenetriaminepentacetic acid (DTPA) or ethylenediaminetetraacetic acid (EDTA).

The antibodies, derivatives and analogs thereof, and peptides also can be detectably labeled by coupling to a chemiluminescent compound. The presence of the chemiluminescent-tagged peptides are then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibodies, derivatives and analogs thereof, and peptides of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

4.3. Methods of Asministration

The molecules that are determined to specifically bind β PDGFR can be administered to a patient at diagnostically effective doses to detect fibrosis. A diagnostically effective dose refers to that amount of the molecule sufficient to target a diagnostic to a cell containing β PDGFR on its surface such that the cell can be detected using methods commonly available in the art, e.g., as described in Section 4.4.1 supra.

4.3.1. Effective Dose

Toxicity and diagnostic efficacy of such molecules can be determined by standard pharmaceutical procedures in cell cultures or experimental animals, e.g., for determining the $LD_{50}$ (the dose lethal to 50% of the population).

The data obtained from the cell culture assays and animal studies can be used in formulating a range of dosage for use in humans. For example, animal model systems can be used to assay for doses effective to visualize fibrotic lesions using the labeled molecules. The dosage of such compounds lies preferably within a range of circulating concentrations with little or no toxicity. The precise dose to be employed in the formulation will depend on the route of administration and the seriousness of the disease, and should be decided according to the judgment of the practitioner and each patient's circumstances. However, suitable dosage ranges for intravenous administration are generally about 1.0 to 20 micrograms of compound per kilogram body weight. Levels in plasma may be measured, for example, by high performance liquid chromatography.

4.3.2. Formulations and Use

Pharmaceutical compositions for use in accordance with the present invention may be formulated in conventional manner using one or more physiologically acceptable carriers or excipients.

Methods of administration include but are not limited to intravenous, subcutaneous, intraperitoneal, and intradermal routes. Administration can be systemic or local. In a specific embodiment, it is desirable to administer the pharmaceutical compositions of the invention locally by direct injection at the site (or former site) of a malignant tumor or fibrotic tissue.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The invention also provides a pharmaceutical pack or kit comprising one or more containers filled with one or more of the ingredients of the pharmaceutical compositions of the invention.

4.4. Diagnosis and Imaging of Fibrosis

Labeled antibodies, derivatives and analogs thereof, and peptides and peptide mimetics which specifically bind to a β PDGFR can be used for diagnostic purposes to detect, diagnose, or monitor fibrosis. In a preferred embodiment, the molecules of the invention can be used for diagnostic purposes to detect, diagnose, or monitor fibrosis, in particular hepatic fibrosis.

In a preferred embodiment, fibrosis are detected in the patient. The patient is an animal and is preferably a human.

In an embodiment, diagnosis is carried out by: a) administering to a subject an effective amount of a labeled molecule which specifically binds to a β PDGFR; b) delaying detecting for a time interval following the administering for permitting the labeled molecule to preferentially concentrate in any fibrotic lesions in the subject and for unbound labeled molecule to be cleared to background level; c) determining background level; and d) detecting the labeled molecule in the subject, such that detection of labeled molecule above the background level indicates the presence of a fibrotic lesion. Background level can be determined by various methods including: measuring the amount of labeled molecule in tissue which does not normally express β PDGFR, e.g., muscle, either in the subject being diagnosed or in a second subject not suspected of having fibrotic tissue; or comparing the amount of labeled molecule detected to a standard value previously determined for a particular system.

Depending on several variables, including the type of label used and the mode of administration, the time interval following the administering for permitting the labeled molecule to preferentially concentrate in any fibrotic lesions in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the fibrosis is carried out by repeating the method for diagnosing the fibrosis, for example, one month after initial diagnosis, six months after initial diagnosis, one year after initial diagnosis, etc.

4.4.1. Methods of Detection and Imaging

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include but are not limited to: computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument.

4.5. Therapeutic Uses

The invention provides for treatment of various cancers by administration of a therapeutic compound (termed herein "Therapeutic"). Such Therapeutics include but are not limited to: antibodies, derivatives and analogs thereof, and peptides and peptide mimetics which specifically bind to a β PDGFR (as described hereinabove).

In a preferred embodiment, a cytotoxic or cytostatic compound, including but not limited to: saporin, A-chain ricin, A-chain cholera toxin, an antibiotic, an antimetabolite, is coupled to the Therapeutic.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A method for detecting one or more fibrotic lesions in a liver or lung of a subject comprising:
   a) administering to the subject an effective amount of a labeled molecule which specifically binds to a β PDGFR;
   b) delaying detecting for a time interval following the administration for permitting the labeled molecule to preferentially concentrate at any fibrotic lesion in the liver or lung of the subject and for unbound labeled molecule to be cleared to background level;

c) determining the background level; and d) detecting the labeled molecule in the liver or lung of the subject, wherein detection of the labeled molecule in the liver or lung of the subject above the background level indicates the presence of a fibrotic lesion in the liver or lung.

2. The method of claim 1 in which the subject is a human.

3. The method of claim 1 in which the molecule is an antibody to a β PDGFR or a portion of said antibody containing the binding domain thereof.

4. The method of claim 1 in which the molecule is a humanized antibody.

5. The method of claim 1 in which the labeled molecule is labeled with a radioisotope.

6. The method of claim 1 in which the labeled molecule is detected in vivo.

7. The method of claim 1 in which the time interval is 6 hours to 48 hours.

8. The method of claim 1 in which the labeled molecule is administered intravenously.

9. The method of claim 1 which further comprises repeating steps (a) through (d) at monthly intervals.

10. The method of claim 1 wherein the fibrotic lesion is in the liver.

11. The method of claim 10 wherein the fibrotic lesion results from a chronic hepatitis C virus infection, a chronic hepatitis B virus infection, or cirrhosis.

12. A method for detecting one or more fibrotic lesions in a liver or lung of a subject, comprising imaging said subject at a time interval after administering to said subject an effective amount of a labeled molecule which specifically binds to a β PDGFR, said time interval being sufficient to permit the labeled molecule to preferentially concentrate at any fibrotic lesion in the liver or lung of said subject and for unbound labeled molecule to be cleared to background level, wherein detection of the labeled molecule in the liver or lung of the subject above the background level indicates the presence of a fibrotic lesion in the liver or lung.

13. The method of claim 12 in which the subject is a human.

14. The method of claim 12 in which the molecule is an antibody to a β PDGFR or a portion of said antibody containing the binding domain thereof.

15. The method of claim 12 in which the molecule is a humanized antibody.

16. The method of claim 12 in which the labeled molecule is labeled with a radioisotope.

17. The method of claim 12 in which the time interval is 6 hours to 48 hours.

18. The method of claim 12 wherein the fibrotic lesion is in the liver.

19. The method of claim 18 wherein the fibrotic lesion results from a chronic hepatitis C virus infection, a chronic hepatitis B virus infection, or cirrhosis.

* * * * *